United States Patent
Mortensen

(10) Patent No.: US 9,690,958 B2
(45) Date of Patent: Jun. 27, 2017

(54) REGISTRATION OF MEDICAL EQUIPMENT

(71) Applicant: Caretag Surgical ApS, Horsholm (DK)

(72) Inventor: Soren Bilsoe Mortensen, Espergaerde (DK)

(73) Assignee: Caretag Surgical ApS, Horsholm (DK)

( * ) Notice: Subject to any disclaimer, the term of this patent is extended or adjusted under 35 U.S.C. 154(b) by 0 days.

(21) Appl. No.: 14/911,259

(22) PCT Filed: Aug. 7, 2014

(86) PCT No.: PCT/EP2014/067003
§ 371 (c)(1),
(2) Date: Feb. 9, 2016

(87) PCT Pub. No.: WO2015/018902
PCT Pub. Date: Feb. 12, 2015

(65) Prior Publication Data
US 2016/0196456 A1     Jul. 7, 2016

(30) Foreign Application Priority Data
Aug. 9, 2013 (EP) .................................. 13179879

(51) Int. Cl.
*G06K 7/10* (2006.01)
*H01Q 1/52* (2006.01)
(Continued)

(52) U.S. Cl.
CPC ........ *G06K 7/10178* (2013.01); *B62B 5/0096* (2013.01); *G06F 19/327* (2013.01);
(Continued)

(58) Field of Classification Search
CPC .......... G06K 19/07327; G06K 19/005; G06K 19/025; G06K 19/07749; B62B 5/0096;
(Continued)

(56) References Cited

U.S. PATENT DOCUMENTS 6,320,509 B1    11/2001   Brady et al.
7,839,276 B2 *   11/2010   Rodgers ................ G06F 21/606
                                                             340/501

(Continued)

FOREIGN PATENT DOCUMENTS

EP      1487126 A1    12/2004
EP      1688863 A1     9/2006

(Continued)

OTHER PUBLICATIONS

International Search Report dated Oct. 16, 2014, issued in PCT Application No. PCT/EP2014/067003, filed Aug. 7, 2014 (3 pgs.).

*Primary Examiner* — Dionne H Pendleton
(74) *Attorney, Agent, or Firm* — Knobbe, Martens, Olson & Bear, LLP

(57) ABSTRACT

An RFID registration apparatus for registering units comprising RFID tags. The registration apparatus comprises: a detector space defined by a top, a bottom and four vertical sides including a first vertical side and a second vertical side, wherein the second vertical side is opposite the first vertical side; a receiver adapted to receive a number of units and be placed inside the detector space; a first antenna configured for reading RFID tags by emitting and receiving electromagnetic radiation within a first frequency range; and at least four plane reflector surfaces. Wherein a first primary reflector surface and a first secondary reflector surface span a first angle, and a second primary reflector surface and a second secondary reflector surface span a second angle. The first angle and the second angle are in the range of 70-140 degrees.

15 Claims, 5 Drawing Sheets

(51) Int. Cl.
| | |
|---|---|
| *B62B 5/00* | (2006.01) |
| *G06K 7/00* | (2006.01) |
| *H01Q 1/22* | (2006.01) |
| *H01Q 19/185* | (2006.01) |
| *G06F 19/00* | (2011.01) |

(52) U.S. Cl.
CPC ......... *G06K 7/0008* (2013.01); *H01Q 1/2216* (2013.01); *H01Q 1/526* (2013.01); *H01Q 19/185* (2013.01); *H04Q 2209/47* (2013.01); *H04Q 2209/75* (2013.01)

(58) Field of Classification Search
CPC ........ B62B 3/1424; H01Q 1/22; H01Q 1/526; H01Q 1/2216; G06F 21/606; G06Q 20/10; G06Q 20/18; G06Q 20/342; G06Q 30/00; G06Q 30/0215; G06Q 30/06; G07F 17/329; G07F 7/0636; H04K 2203/20; H04K 3/68; H04K 3/825; H04K 3/86; H04W 4/14; Y10S 194/905; H04Q 2209/47

See application file for complete search history.

(56) References Cited

U.S. PATENT DOCUMENTS

| | | |
|---|---|---|
| 2005/0156806 A1 | 7/2005 | Ohta et al. |
| 2006/0158334 A1 | 7/2006 | Chang |
| 2006/0278706 A1 | 12/2006 | Hatakeyama et al. |
| 2011/0036738 A1 | 2/2011 | Hiltl |
| 2011/0095892 A1 | 4/2011 | Hong et al. |
| 2012/0007718 A1* | 1/2012 | Lee ............. G01S 3/38 340/10.4 |
| 2012/0169470 A1 | 7/2012 | Lee |

FOREIGN PATENT DOCUMENTS

| | | |
|---|---|---|
| WO | 2007024348 A2 | 3/2007 |
| WO | 2011072844 A1 | 6/2011 |

* cited by examiner

REGISTRATION OF MEDICAL EQUIPMENT

CROSS REFERENCE TO RELATED APPLICATIONS

This application is the U.S. National Phase Application under 35 U.S.C. §371 of International Application No. PCT/EP2014/067003, filed 7 Aug. 2014, designating the U.S. and published as WO2015/018902 on 12 Feb. 2015 which claims the benefit of European Patent Application No. EP 13179879.5, filed 9 Aug. 2013. Any and all applications for which a foreign or a domestic priority is claimed is/are identified in the Application Data Sheet filed herewith and is/are hereby incorporated by reference in their entirety under 37 C.F.R. §1.57.

BACKGROUND

Technical Field

The present invention relates to a device for automatically detecting and registering medical equipment such as utensils, disposables and/or surgical instruments, especially for registering surgical instruments before and after an operation, or before and after sterilization.

Description of the Related Art

In an operating room, both certain surgical instruments and a certain number of instruments may be needed to perform a surgical procedure. Typically the instruments brought into the operating room prior to an operation is counted and registered manually, to be certain that the right amount and correct instruments are available for operation. After completion of the operation, the instruments are again counted and registered manually, to ensure that no instruments are missing.

Manually registering and counting of equipment, before and after a surgery, is both time consuming and ineffective. Further, the consequence of errors may in a worst case scenario pose a life threatening situation for the patient.

Other situations exist where medical instruments need to be registered, and where a more efficient procedure will be beneficial, e.g. before and after sterilization, in or out of maintenance etc.

Radio-frequency identification (RFID) may comprise passive chips, or "tags" as it is more commonly known, which essentially are small radio transceivers powered by the electromagnetic field emitted by an antenna. The received energy is used to transmit the content of a memory. Hence, the tag itself does not comprise a power source such as a battery.

Passive RFID tags may be in sizes of millimeters, and may be reliably read from a distance of a couple of meters. However, these sizes and ranges are continuously improved. The reading range also depends on a number of factors such as surrounding material, orientation of the tag, transmission power of the antenna, number of tags etc.

In the following, RFID tags will mainly be thought of as passive RFID tags. However, most apparatuses may be realized in ways of utilizing passive as well as active RFID tags.

Providing the available instruments with an RFID tag, it is in theory possible, within a couple of seconds, to read the presence of all RFID tags, and thus all instruments present in a defined space. However, several problems occur since an instrument itself, neighboring instruments, the tray and several other things may all provide shielding, scattering and/or diffusion of the signal. This means that the precision of the registration procedure may be compromised. Thus, there is a need for inventions that will provide high precision and reliability of registering units such as medical instruments, comprising RFID.

Applications have been proposed having a plurality of reflector surfaces, such as the radio communication system disclosed in US 2006/0278706 A1 comprising a plurality of reflecting plates in a space where a plurality of RFID tags are accumulated. The reflecting plates of US 2006/02878706 direct traveling direction of the radio wave irradiated from the reader/writer towards the RFID tags. However, the method described by US 2006/0278706 performs poorly if the RFID tags are randomly distributed within the space.

SUMMARY

There is a need for a device that automatically and quickly detects, register and/or count the medical instruments brought into and out from an operating room.

Despite the known solutions there is still a need for an apparatus that is able, in a consistent manner, to detect and register medical instruments.

Likewise other units, such as bags of blood, disposables etc, can also be subjected to quick and precise registering according to the claimed method and/or in the claimed apparatus.

Accordingly, an RFID registration apparatus for registering units comprising RFID tags is provided, the registration apparatus comprising: a detector space defined by a top, a bottom and four vertical sides including a first vertical side and a second vertical side, wherein the second vertical side is opposite the first vertical side; a receiver adapted to receive a number of units and be placed inside the detector space; a first antenna configured for reading RFID tags by emitting and receiving electromagnetic radiation within a first frequency range, the first antenna is at the top of the detector space; and at least four plane reflector surfaces, including a first primary reflector surface, a first secondary reflector surface, a second primary reflector surface and a second secondary reflector surface, each reflector surface is adapted to reflect electromagnetic radiation within the first frequency range, wherein the first primary reflector surface is adjacent to, i.e. positioned to intersect, the first vertical side and the top of the detector space, and the first secondary reflector surface is adjacent to, i.e. positioned to intersect, the first vertical side and the bottom of the detector space, and the second primary reflector surface is adjacent to, i.e. positioned to intersect, the second vertical side and the top of the detector space, and the second secondary reflector surface is adjacent to, i.e. positioned to intersect, the second vertical side and the bottom of the detector space. Wherein the first primary reflector surface and the first secondary reflector surface span a first angle facing the detector space, and the second primary reflector surface and the second secondary reflector surface span a second angle facing the detector space, wherein the first angle and the second angle are less than 180 degrees, such as in the range of 70-140 degrees.

The first angle and/or the second angle may be in the range of 80-130 degrees.

The first angle and/or the second angle may be a right angle.

The first primary reflector surface and the first antenna may span a first antenna angle facing the detector space, and the second primary reflector surface and the first antenna may span a second antenna angle facing the detector space, wherein the first antenna angle and/or the second antenna angle may be more than 90 degrees.

The first primary reflector surface and/or the second primary reflector surface may extend to a vertical position above the top of the detector space.

The first secondary reflector surface and/or the second secondary reflector surface may extend to a vertical position below the bottom of the detector space.

The receiver may be vertically positioned below a line from the first angle to the second angle.

The RFID registration apparatus may comprise a first motor configured to drive the receiver into and/or out of the detector space.

The RFID registration apparatus may comprise a second motor configured to change the orientation of the first antenna when reading RFID tags.

The first antenna may be tilted when reading RFID tags.

The first antenna may be rotated when reading RFID tags.

The RFID registration apparatus may comprise a second antenna, the second antenna may be adjacent to, i.e. positioned to intersect, the top and a third vertical side of the detector space.

The first frequency range may be in the range of 860-960 MHz.

The units for registration may be medical equipment, such as surgical instruments, bags of blood, disposables etc.

Also disclosed is a method for detecting and registering units comprising RFID tags, adapted to respond to receiving electromagnetic radiation within a first frequency range, the method comprising the steps:

a. place a number of units in a receiver, each unit comprising an RFID tag;
b. place the receiver inside a detector space, the detector space being defined by a top, a bottom and four vertical sides including a first vertical side and a second vertical side, wherein the second vertical side is opposite the first vertical side, and adjacent to the detector space is at least four plane reflector surfaces, including a first primary reflector surface, a first secondary reflector surface, a second primary reflector surface and a second secondary reflector surface, each reflector surface being adapted to reflect electromagnetic radiation within the first frequency range, wherein the first primary reflector surface is adjacent to, i.e. positioned to intersect, the first vertical side and the top of the detector space, and the first secondary reflector surface is adjacent to, i.e. positioned to intersect, the first vertical side and the bottom of the detector space, and the second primary reflector surface is adjacent to, i.e. positioned to intersect, the second vertical side and the top of the detector space, and the second secondary reflector surface is adjacent to, i.e. positioned to intersect, the second vertical side and the bottom of the detector space, and a first antenna is at the top of the detector space, the first antenna being configured for reading RFID tags by emitting and receiving electromagnetic radiation within the first frequency range, the first primary reflector surface and the first secondary reflector surface span a first angle facing the detector space, and the second primary reflector surface and the second secondary reflector surface span a second angle facing the detector space, wherein the first angle and the second angle are less than 180 degrees, such as in the range of 70-140 degrees;
c. emit electromagnetic radiation within the first frequency range from the first antenna;
d. receive at the first antenna responses from RFID tags in the receiver in the form of electromagnetic radiation;
e. repeat steps c and d a number of times;
f. identify from the received responses which RFID tags responded; and
g. remove the receiver from the detector space.

The first antenna may be tilted and/or rotated during the repeated emitting and receiving of electromagnetic radiation.

The tilt of the first antenna may have a range of motion in the range of 5 to 60 degrees.

The method may further comprise comparing the identified RFID tags with values of a table, and reporting whether or not the identified RFID tags corresponds to values of the table.

The first frequency range may be in the range of 860-960 MHz.

The method may further comprise driving the receiver in and/or out of the detector space by use of a first motor.

The receiver may be repositioned during the repeated emitting and receiving of electromagnetic radiation.

Further disclosed is, an assembly comprising units supplied with an RFID tag and an RFID registration apparatus in accordance with the present invention.

The inventors of the present invention have found that, specific respective orientations of reflecting plates enhance readability of RFID tags being at random locations within a detector space.

It is an advantage of the present invention that units may be registered automatically, quickly and reliable, hence an operation can be initiated faster, and the risk of potential life threatening mistakes are greatly reduced.

According to another aspect of the invention, an RFID registration apparatus for registering units comprising RFID tags is provided, the registration apparatus comprising: a detector space defined by a top, a bottom and four vertical sides including a first vertical side and a second vertical side, wherein the second vertical side is opposite the first vertical side; a receiver adapted to receive a number of units and be placed inside the detector space; a first antenna configured for reading RFID tags by emitting and receiving electromagnetic radiation within a first frequency range, the first antenna is at the top of the detector space; and at least four plane reflector surfaces, including a first primary reflector surface, a first secondary reflector surface, a second primary reflector surface and a second secondary reflector surface, each reflector surface is adapted to reflect electromagnetic radiation within the first frequency range, wherein the first primary reflector surface is adjacent to the first vertical side and the top of the detector space, and the first secondary reflector surface is adjacent to the first vertical side and the bottom of the detector space, and the second primary reflector surface is adjacent to the second vertical side and the top of the detector space, and the second secondary reflector surface is adjacent to the second vertical side and the bottom of the detector space. Wherein the first primary reflector surface and the first secondary reflector surface span a first angle facing the detector space, and the second primary reflector surface and the second secondary reflector surface span a second angle facing the detector space, wherein the first angle and the second angle are less than 180 degrees, such as in the range of 70-140 degrees.

According to yet another aspect of the invention, an RFID registration apparatus for registering units comprising RFID tags is provided, the registration apparatus comprising: a detector space defined by a top, a bottom and four vertical sides including a first vertical side and a second vertical side, wherein the second vertical side is opposite the first vertical side; a receiver adapted to receive a number of units and be placed inside the detector space; a first antenna configured for reading RFID tags by emitting and receiving electromagnetic radiation within a first frequency range, the first antenna is at the top of the detector space; and at least four plane reflector surfaces, including a first primary reflector surface, a first secondary reflector surface, a second primary reflector surface and a second secondary reflector surface, each reflector surface is adapted to reflect electromagnetic radiation within the first frequency range, wherein the first primary reflector surface is positioned to intersect, the first vertical side and the top of the detector space, and the first secondary reflector surface is positioned to intersect the first vertical side and the bottom of the detector space, and the second primary reflector surface is positioned to intersect the second vertical side and the top of the detector space, and the second secondary reflector surface is positioned to intersect the second vertical side and the bottom of the detector space. Wherein the first primary reflector surface and the first secondary reflector surface span a first angle facing the detector space, and the second primary reflector surface and the second secondary reflector surface span a second angle facing the detector space, wherein the first angle and the second angle are less than 180 degrees, such as in the range of 70-140 degrees.

It is envisaged that any embodiments or elements as described in connection with any one aspect may be used with any other aspects or embodiments, mutatis mutandis.

BRIEF DESCRIPTION OF THE DRAWINGS

The above and other features and advantages of the present invention will become readily apparent to those skilled in the art by the following detailed description of exemplary embodiments thereof with reference to the attached drawings, in which.

The figures are schematic and simplified for clarity, and they merely show details which are essential to the understanding of the invention, while other details have been left out. Throughout, the same reference numerals are used for identical or corresponding parts.

DETAILED DESCRIPTION

Figure 1:
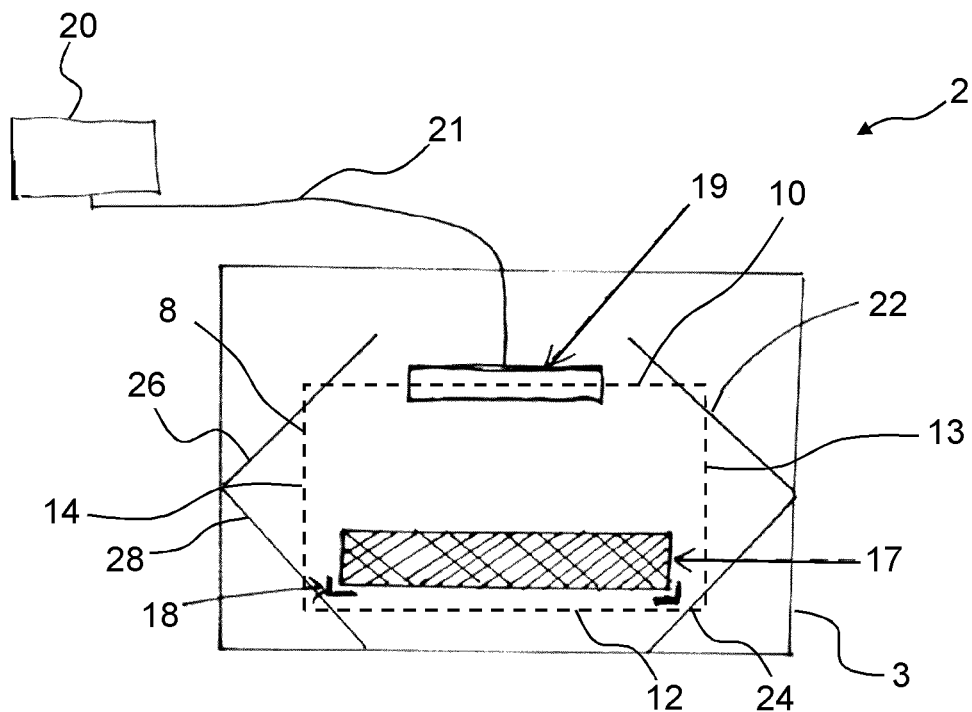
FIG. 1 schematically illustrates a front view of an exemplary RFID registration apparatus.

The present invention relates to registration of units comprising radio-frequency identification (RFID). In particular the present invention relates to an RFID registration apparatus for registering units comprising RFID tags.

The units for registration may be medical equipment, such as surgical instruments, bags of blood, disposables etc.

RFID tags will mainly be thought of as passive RFID tags. However, the disclosed apparatus may be realized in ways of utilizing passive as well as active RFID tags. Hence, the word "RFID tag" is used throughout the description and comprises all types of RFID tags. The words "RFID tag" and "tag" may be used interchangeably.

Units may have RFID tags provided by the manufacturer, or the RFID tag may be glued to existing units. Before use, the units may be stored in a metal tray which might be placed in the receiver adapted to be placed inside the detector space The number of units to be registered is determined by the size of the apparatus. The number of units may vary from a few units i.e. less than 10 to above 100. Typically the number of units will be less than 200 instruments, such as less than 150 units, such as less than 100 units, such as less than 50 units.

The size of the apparatus may vary from less than a meter in each direction, to several meters in each direction. An upper limit of the size is set by the reading distance of the RFID tags, i.e. passive RFID tags will have a limited reading range of a couple of meters, whereas active RFID tags will have a longer reading range. A lower limit of the size is set by the desire to register many units and the physical dimensions of the devices of the apparatus, i.e. antenna, receiver etc.

Generally the size of the apparatus is thought to be less than 2 meters×2 meters×2 meters.

The registration apparatus may comprise a housing, wherein the housing defines an outer casing for containing the functional parts of the registration apparatus.

The registration apparatus comprises a detector space that is not to be interpreted as a space defined by physical i.e. solid walls, but merely the space wherein the units are placed when registration is to take place. The detector space may thus be defined by a "top", a "bottom" and four vertical "sides". The four vertical sides may include a first vertical side, a second vertical side, a third vertical side and a fourth vertical side. The second vertical side may designate the side opposite the first vertical side. The third vertical side may designate the fourth vertical side.

In order to place the units within the detector space, the apparatus may comprise a receiver. The receiver may be adapted to receive a number of units and be placed inside the detector space. "Inside" meaning that the receiver is positioned completely within the detector space, i.e. no parts of the receiver or of the units placed on or in the receiver is positioned outside the sides of the detector space.

The receiver may be constructed as two rails adapted to receive a tray with units. Alternatively the receiver may be constructed as a tray itself.

The "bottom" of the detector space, may be defined as a plane below the receiver, or as just below the receiver.

In an exemplary apparatus the units are placed in a tray, and the one or more tray(s) is/are placed in the receiver. In another exemplary apparatus, the units are placed directly in the receiver.

In order to read the RFID tags, a first antenna may be located at the top of the detector space. The "top" of the detector space, may be defined as a plane above the first antenna, or as below the first antenna, or as just above the first antenna, or as just below the first antenna. The first antenna may be configured to read RFID tags by emitting and receiving electromagnetic radiation within a first frequency range. The first frequency range may be according to standards within the industry. The first frequency range may be in the range between 800 MHz and 1000 MHz, such as in the range between 860 and 960 MHz, such as in the range between 860 MHz and 870 MHz, or such as in the range between 900 MHz and 930 MHz.

The first antenna may have certain antenna characteristics, such as certain radiation pattern and polarization.

The radiation pattern of the first antenna may be such that transmission in the direction of the receiver, containing the RFID tags, is optimized.

The polarization of the first antenna may be any elliptical polarization or a linear polarization. The polarization of the first antenna may be such that different orientations of the RFID tags are accounted for, such as circular polarization.

The first antenna may have a field of view of more than 200 degrees such as more than 230 degrees, such as more than 250 degrees, such as more than 270 degrees The registration apparatus may comprise a second antenna for the purpose of emitting electromagnetic radiation with different polarization and radiation patterns. Thus, the apparatus is able to receive a more reliable result of the registration.

The second antenna may be right hand circular polarized, and the first antenna may be left hand circular polarized, or vice versa, i.e. the first and second antennas may be opposite circular polarized.

In an exemplary registration apparatus the first antenna is placed at the top of the detector space, and the second antenna is placed adjacent to, i.e. positioned to intersect, the top and the third vertical side of the detector space.

The first antenna may be coupled to a reader by a wire, or the reader and the first antenna may be integrated into a single unit. The reader may be located outside the housing of the registration apparatus.

The second antenna may be coupled to the reader by a second wire.

The apparatus may comprise at least four plane reflector surfaces. The four reflector surfaces may include a first primary reflector surface, a first secondary reflector surface, a second primary reflector surface and a second secondary reflector surface.

Each reflector surface may be adapted to reflect electromagnetic radiation within the first frequency range. This may be achieved by covering the surfaces with material configured to reflect electromagnetic radiation within the first frequency range. The reflecting material may be such as a foil made of aluminum or a polymer, or it may comprise a combination of different materials, e.g. aluminum, polyethylene (PE) and polyethylene terephthalate (PET). The reflecting material may be such as Nova-Guard® RFID Shielding Foil.

A fifth reflector surface may be applied below the receiver. The fifth reflector surface may be a horizontal surface. The fifth reflector surface may form part of the housing of the registration apparatus.

The first primary reflector surface may be placed adjacent to, i.e. positioned to intersect, the first vertical side and the top of the detector space. The first secondary reflector surface may be placed adjacent to, i.e. positioned to intersect, the first vertical side and the bottom of the detector space. Thus, the first primary and the first secondary reflector surface may be adjacent to the same side of the detector space. And the first primary reflector surface may be placed vertically above the second primary reflector surface.

The second primary reflector surface may be placed adjacent to, i.e. positioned to intersect, the second vertical side and the top of the detector space. The second secondary reflector surface may be placed adjacent to, i.e. positioned to intersect, the second vertical side and the bottom of the detector space. Thus, the second primary and the second secondary reflector surface may be adjacent to the same side of the detector space. And the second primary reflector surface may be placed vertically above the second primary reflector surface.

The second vertical side of the detector space is opposite the first vertical side of the detector space. Thus, the first reflector surfaces and the second reflector surfaces are adjacent opposite sides of the detector space.

The meaning of the word "adjacent" may refer to elements having at least a single point in common, i.e. an element is positioned to intersect with another element. Thus, placing an element, e.g. reflector surface, adjacent to two sides of the detector space imply that the element is positioned to intersect the two sides. An intersection between elements is regarded as the point or line where the elements meet or cross. An element, e.g. reflector surface, may be positioned at the intersection between two sides in order to intersect with the two sides.

For example, the intersection between the top of the detector space and the first vertical side of the detector space is regarded as the line where the top and the first vertical side meet. The first primary reflector surface may be placed to intersect the first vertical side and the top of the detector space. The first primary reflector surface may be positioned such that the intersection between the first primary reflector surface and the first vertical side, the intersection between the first primary reflector surface and the top, and the intersection between the first vertical side and the top, are coinciding.

For example, the intersection between the bottom of the detector space and the first vertical side of the detector space is regarded as the line where the bottom and the first vertical side meet. The first secondary reflector surface may be placed to intersect the first vertical side and the bottom of the detector space. The first secondary reflector surface may be positioned such that the intersection between the first secondary reflector surface and the first vertical side, the intersection between the first secondary reflector surface and the bottom, and the intersection between the first vertical side and the bottom, are coinciding.

For example, the intersection between the top of the detector space and the second vertical side of the detector space is regarded as the line where the top and the second vertical side meet. The second primary reflector surface may be placed to intersect the second vertical side and the top of the detector space. The second primary reflector surface may be positioned such that the intersection between the second primary reflector surface and the second vertical side, the intersection between the second primary reflector surface and the top, and the intersection between the second vertical side and the top, are coinciding.

For example, the intersection between the bottom of the detector space and the second vertical side of the detector space is regarded as the line where the bottom and the second vertical side meet. The second secondary reflector surface may be placed to intersect the second vertical side and the bottom of the detector space. The second secondary reflector surface may be positioned such that the intersection between the second secondary reflector surface and the second vertical side, the intersection between the second secondary reflector surface and the bottom, and the intersection between the second vertical side and the bottom, are coinciding.

A first angle is spanned between the first primary and the first secondary reflector surfaces. The first angle is measured on the side of the reflector surfaces facing the detector space. The first angle may be less than 180 degrees. The first angle may in an exemplary apparatus be in the range of 70-140 degrees, or in the range of 80-130 degrees, or in the range of 80-120 degrees. The first angle may be substantially right angled, such as 90 degrees.

Similarly, a second angle is spanned between the second primary and the second secondary reflector surfaces. The second angle is measured on the side of the reflector surfaces facing the detector space. The second angle may be less than 180 degrees. The second angle may in an exemplary apparatus be in the range of 70-140 degrees, or in the range of 80-130 degrees, or in the range of 80-120 degrees. The second angle may be substantially right angled, such as 90 degrees.

The first angle and the second angle may be substantially equal.

The first primary and the first secondary reflector surfaces may abut. Alternatively first primary and the first secondary reflector surface may not abut, but leave an open section between them or being joined together by an arbitrary structure e.g. a non-planar part such as a curved surface.

The second primary and the second secondary reflector surfaces may abut. Alternatively second primary and the second secondary reflector surface may not abut, but leave an open section between them or being joined together by an arbitrary structure e.g. a non-planar part such as a curved surface.

The first primary reflector surface and the first antenna may span a first antenna angle. The first antenna angle is measured relative to the sides of the first antenna and the first primary reflector surface facing the detector space. The first antenna angle may be more than 90 degrees, e.g. more than 100 degrees, or more than 110 degrees, or more than 120 degrees, or more than 130 degrees. The first antenna angle may be less than 150 degrees. The first antenna angle may be in the range of 120 to 140 degrees.

Similarly, the second primary reflector surface and the first antenna may span a second antenna angle. The second antenna angle is measured relative to the sides of the first antenna and the second primary reflector surface facing the detector space. The second antenna angle may be more than 90 degrees, e.g. more than 100 degrees, or more than 110 degrees, or more than 120 degrees, or more than 130 degrees. The second antenna angle may be less than 150 degrees. The second antenna angle may be in the range of 120 to 140 degrees.

The first antenna angle and the second antenna angle may be substantially equal.

The first primary reflector surface and/or the second primary reflector surface may extend to a vertical position above the top of the detector space. The first antenna may be placed at the top of the detector space. Thus, the primary reflector surfaces may extend to a vertical position above the first antenna. By extending the primary reflector surfaces to a vertical position above the first antenna, the electromagnetic radiation transmitted away from the detector space may be reflected and directed towards the detector space and to the RFID tags to be read. Hence the reliability of the reading procedure may be enhanced.

The first secondary reflector surface and/or the second secondary reflector surface may extend to a vertical position below the bottom of the detector space, i.e. below the receiver. The receiver containing the units to be registered is placed inside the detector space. Thus, by extending the secondary reflector surfaces to a vertical position below the detector space, the electromagnetic radiation transmitted away from the detector space may be reflected and directed towards the detector space and to the RFID tags to be read. Hence the reliability of the reading procedure may be enhanced.

Similarly electromagnetic radiation emitted from an RFID tag may have a direction away from the first antenna, by secondary reflector surfaces extending below the bottom of the detector space, i.e. below the receiver, the electromagnetic radiation may be reflected towards the first antenna. Hence, adding to the reliability of the reading procedure.

The receiver may be vertically positioned below a line from the first angle to the second angle. Hence the receiver may be positioned in the bottom part of the detector space. The position of the receiver below the line from the first to the second angle may benefit the reliability of the reading procedure.

Alternatively, the receiver may be vertically positioned below half the distance from the bottom of the detector space to the first antenna.

The RFID registration apparatus may comprise a first motor. The first motor may be configured to drive the receiver into and/or out of the detector space. This may ease operation of the apparatus, and help place the units in an optimal position within the detector space. Further, the second motor may perturb the receiver and thus the units during the reading procedure, further improving the reliability of the reading procedure The RFID registration apparatus may comprise a second motor configured to change the orientation of the first antenna when reading RFID tags. The first antenna may have a polarization and a radiation pattern preventing RFID tags with a certain orientation to receive the electromagnetic signal emitted from the first antenna. The polarization and radiation pattern may be changed by changing the relative orientation between RFID tags and first antenna. Thus, the first antenna may be tilted during the reading procedure.

The tilt of the first antenna may have a range of motion up to 60 degrees, such as in the range of 5 to 60 degrees, such as a range of motion in the range of 10 to 40 degrees or in the range of 20 to 30 degrees.

The tilt of the first antenna may be performed from a start angle to an end angle, wherein the start angle and the end angle are measured relative to the receiver. The receiver may in this respect be positioned horizontal. Hence, the start angle and end angle may be relative to a horizontal position of the first antenna.

The start angle may be in the range of 0 to −45 degrees, such as in the range of −5 to −40 degrees, or in the range of −10 to −30 degrees, or in the range of −15 to −20 degrees.

The end angle may be in the range of 0 to 45 degrees, such as in the range of 5 to 40 degrees, or in the range of 10 to 30 degrees, or in the range of 15 to 20 degrees.

The start angle and the end angle may be of substantially the same magnitude.

The tilt may be around a horizontal axis. The tilt may be performed around a first horizontal axis perpendicular to the first vertical side and/or perpendicular to the second vertical side. Alternatively the tilt may be performed around a second horizontal axis perpendicular to the first horizontal axis.

Alternatively or additionally the first antenna may be rotated during the reading procedure. The first antenna may be rotated 360 degrees, or the first antenna may be rotated with a range of motion in the range of 0-180 degrees, such as in the range of 30-160 degrees or in the range of 50-140 degrees or in the range of 70-120 degrees or in the range of 80-100 degrees, or 90 degrees.

The first antenna may be rotated in one direction followed by a rotation in a second direction, i.e. the first antenna may be rotated clockwise followed by an anti-clockwise rotation, or vice versa.

Tilting and rotation of the first antenna may be performed sequentially, i.e. first the first antenna is tilted then the first antenna is rotated or vice versa. Alternatively, tilting and rotation may be performed simultaneously.

An apparatus, such as an apparatus as described, for detection and/or registration of units comprising RFID tags, may be operated according to a method to be described.

The method may comprise the steps:
a. place a number of units in a receiver, each unit comprising an RFID tag,
b. place the receiver in the detector space,
c. emit electromagnetic radiation within the first frequency range from the first antenna,
d. receive at the first antenna responses from RFID tags in the receiver in the form of electromagnetic radiation,
e. repeat steps c and d a number of times,
f. identify from the received responses which RFID tags responded,
g. remove the receiver from the detector space.

The number of times steps c and d is performed may be any number of times depending on a set time and/or the specification of the reader and antenna used. For example, the number of times steps c and d is performed may be 1 time or more than 1 time, such as more than 5 times, such as more than 25 times, such as more than 50 times, such as more than 100 times.

Steps c and d may be performed simultaneously.

The first antenna may be tilted and/or rotated while performing step e.

The tilt of the first antenna may be performed from the start angle to the end angle as described above. The tilt of the first antenna at step f may have a range of motion in the range of 5 to 60 degrees, such as in the range of 10 to 40 degrees or in the range of 20 to 30 degrees.

The rotation of the first antenna may be performed as described above. The first antenna may be rotated 360 degrees, or the first antenna may be rotated with a range of motion in the range of 0-180 degrees, such as in the range of 30-160 degrees or in the range of 50-140 degrees or in the range of 70-120 degrees or in the range of 80-100 degrees, or 90 degrees.

The apparatus may output a list of identified units. However, it may be beneficial for the operator to be told whether or not the identified units correspond to a predetermined table or list. Thus, the method may further comprise comparing the identified RFID tags with values of a table, and reporting whether or not a comparison criterion has been met or not. The comparison criterion may be that the identified RFID tags correspond to values of the table.

The table may be a table specific to the operation to be performed. Alternatively or additionally it may be the result of an earlier registration, e.g. the registration after operation is compared with the registration that was performed before the operation.

In an exemplary method the apparatus generates a list of detected units and an indication of the comparison criterion.

The method may comprise driving the receiver in to the detector space by use of a first motor, thus placing the receiver in the detector space is achieved by an easy and automatic procedure. Further, the method may comprise driving the receiver out of the detector space when removing the receiver from the detector space.

By utilizing a motor to drive the receiver into and/or out of the detector space, the placement of the receiver may be controlled, and it eases the work of the operator.

The method may comprise a repositioning of the receiver during the repeated emitting and receiving of electromagnetic radiation. The repositioning may be such as an oscillating, vibrating, pulsating and/or reciprocating movement. This may improve the chance of all RFID tags being able to receive and respond to the electromagnetic radiation, thus increasing the reliability of the reading procedure.

DETAILED DESCRIPTION

FIG. 1 schematically illustrates a front view of an exemplary RFID registration apparatus 2. The registration apparatus 2 comprises a housing 3 defining an outer casing of the registration apparatus 2.

The registration apparatus 2 comprises a detector space 8, a receiver 18, a first antenna 19 and four plane reflector surfaces 22, 24, 26, 28 which are found within the housing 3. The reflector surfaces 22, 24, 26, 28 are adapted to reflect electromagnetic radiation within a first frequency range, e.g. by being covered with a material configured to reflect electromagnetic radiation within the first frequency range.

The detector space 8 is an open space, i.e. the detector space is not defined by physical walls, wherein the units 4 (FIG. 2) for registration is placed. The detector space 8 is defined by a top 10, a bottom 12 and four vertical sides. The vertical sides includes a first vertical side 13 and a second vertical side 14, wherein the second vertical side 14 is opposite the first vertical side 13. The bottom 12 of the detector space 8 is defined as a plane just below the receiver 18 and the top of the detector space is defined as a plane at level with the first antenna 19.

The receiver 18 is configured for receiving a number of units. The number of units may be put in a tray 17, which is then placed in the receiver 18. The shown receiver 18 comprises two rails for receiving the tray 17. The receiver places the number of units inside the detector space 8.

The registration apparatus 2 comprises a first antenna 19 connected to a reader 20. The connection between the first antenna 19 and the reader 20 may be by use of a wire 21, or the first antenna 19 and reader 20 may be integrated in a single unit (not shown). The first antenna 19 is placed at the top 10 of the detector space 8. The first antenna 19 is configured to emit electromagnetic radiation within the first frequency range, and configured to receive electromagnetic radiation within the first frequency range, transmitted from RFID tags.

The registration apparatus 2 comprises four plane reflector surfaces, a first primary reflector surface 22, a first secondary reflector surface 24, a second primary reflector surface 26, and a second secondary reflector surface 28.

The first primary reflector surface 22 is placed adjacent to the top 10 and the first vertical side 13 of the detector space 8. The first primary reflector surface 22 is positioned at the intersection between the top 10 and the first vertical side 13.

The first secondary reflector surface 24 is placed adjacent to the bottom 12 and the first vertical side 13 of the detector space 8. The first secondary reflector surface 24 is positioned to intersect the bottom 12 and the first vertical side 13.

The second primary reflector surface 26 is placed adjacent to the top 10 and the second vertical side 14 of the detector space 8. The second primary reflector surface 26 is positioned to intersect the top 10 and the second vertical side 14.

The second secondary reflector surface 28 is placed adjacent to the bottom 12 and the second vertical side 14 of the detector space 8. The second secondary reflector surface 28 is positioned to intersect the bottom 12 and the second vertical side 14.

In FIG. 1 the detector space is illustrated as having two points in common with each reflector surface 22, 24, 26 and 28, but the detector space can also have a single point in common with each reflector surface, or it may have a single point in common with some reflector surfaces while having two points in common with other reflector surfaces.

In FIG. 1, the first antenna 19 is positioned within a space confined by the reflector surfaces 22, 24, 26, 28. Furthermore, the receiver 18 is positioned within the space confined by the reflector surfaces 22, 24, 26, 28.

Figure 1A:
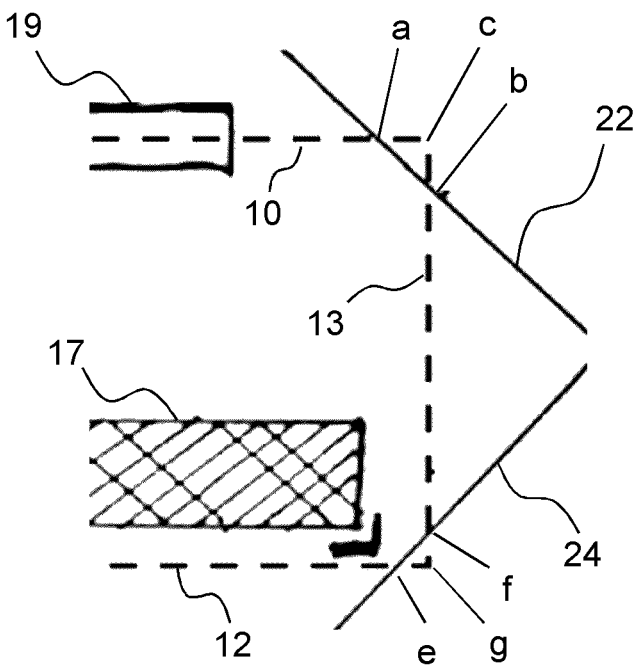
FIG. 1A illustrates a close up of a section of FIG. 1.

FIG. 1A illustrates a close up of a section of FIG. 1 and illustrates intersections between the top 10, the first vertical side 13, the bottom 12 and the first primary reflector surface 22 and the first secondary reflector surface 24. Even though not specifically illustrated, it is emphasized that a similar description may be given in respect of any other side and/or reflector surface.

The intersection between the top 10 and the first primary reflector surface 22 is denoted a. The intersection between the first vertical side 13 and the first primary reflector surface 22 is denoted b. The intersection between the first vertical side 13 and the top 10 is denoted c. It is seen that the first primary reflector surface 22 is placed at the intersection between the first vertical side 13 and the top 10 denoted by c. The intersections a, b, and c may be coinciding. Since the walls defining the detector space 8 are not physical walls, but merely used to define the detector space 8, it will be understood that the first vertical side 13 and/or the top 10 may be chosen such that a, b, and c are coinciding.

The intersection between the bottom 12 and the first secondary reflector surface 24 is denoted e. The intersection between the first vertical side 13 and the first secondary reflector surface 24 is denoted f. The intersection between the first vertical side 13 and the bottom 12 is denoted g. It is seen that the first secondary reflector surface 24 is placed at the intersection between the first vertical side 13 and the bottom 10 denoted by g. The intersections e, f, and g may be coinciding. Since the walls defining the detector space 8 are not physical walls, but merely used to define the detector space 8, it will be understood that the first vertical side 13 and/or the bottom 12 may be chosen such that e, f, and g are coinciding.

Figure 2:
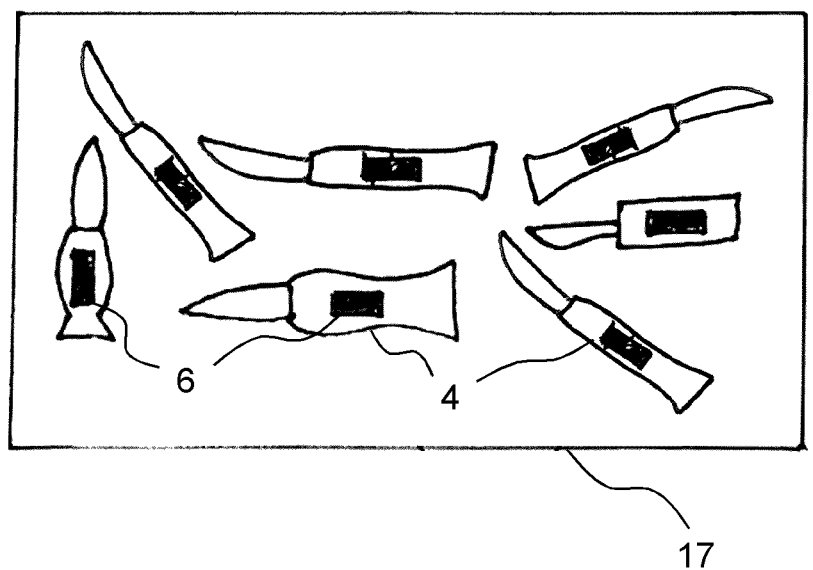
FIG. 2 schematically illustrates a tray comprising exemplary units comprising RFID tags, FIG. 3 schematically illustrates a side view of an exemplary RFID registration apparatus, FIG. 4 schematically illustrates a top view of an exemplary RFID registration apparatus, FIG. 5 schematically illustrates angles of an exemplary RFID registration apparatus.

FIG. 2 illustrates a tray 17 comprising exemplary units 4 each comprising a RFID tags 6. The units 4 as illustrated are 7 lancets that are fitted with RIFD tags 6 on the handle, the number of units 4 can be any number of units 4, and can be several different types of units. The units 4 are randomly placed within the tray 17.

Figure 3:
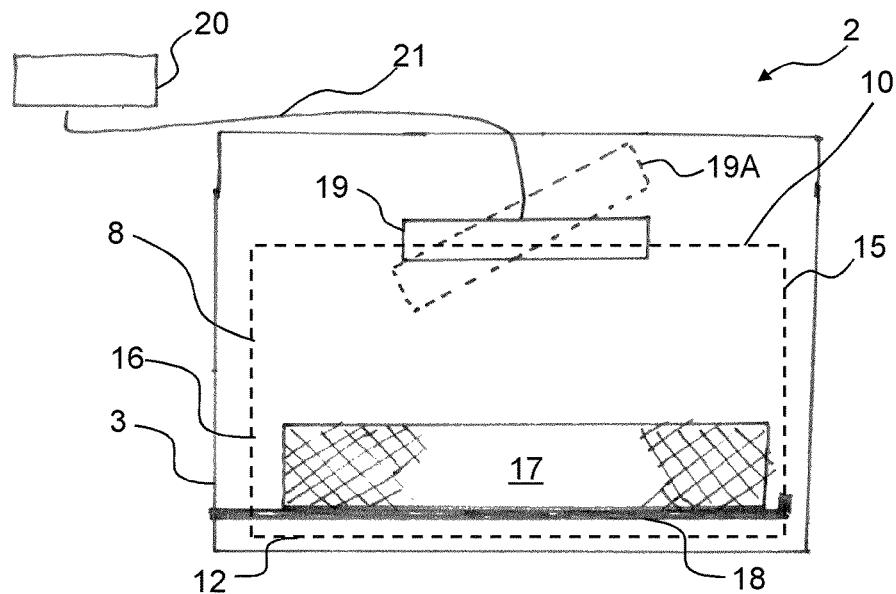

FIG. 3 schematically illustrates a side view of an exemplary RFID registration apparatus 2. In FIG. 3 the detector space 8 is seen with the top 10, the bottom 12, the third vertical side 15 and the fourth vertical side 16. The reflector surfaces are not shown in this figure as the reflector surfaces are placed respectively behind and in front of the receiver 18. The first antenna 19 may be tilted to the position shown with dotted lines as 19A. This may be accomplished by utilizing a motor (not shown) for tilting the first antenna 19. The first antenna 19 may be tilted with a range of motion up to 60 degrees, e.g. starting at an angle in the range of −3 to −30 degrees and ending at an angle in the range of 3 to 30 degrees in respect to horizontal. Tilting the first antenna 19 allows for a dynamic change of the radiation pattern and/or polarization, thus minimizing the risk of RFID tags being orientated in a manner not receiving the electromagnetic radiation. Hence tilting the first antenna 19 increases the precision and reliability of the reading even further. The tilt is in FIG. 3 shown to be around a horizontal axis perpendicular to the first vertical side. However, the tilt may be performed around any horizontal axis.

Figure 4:
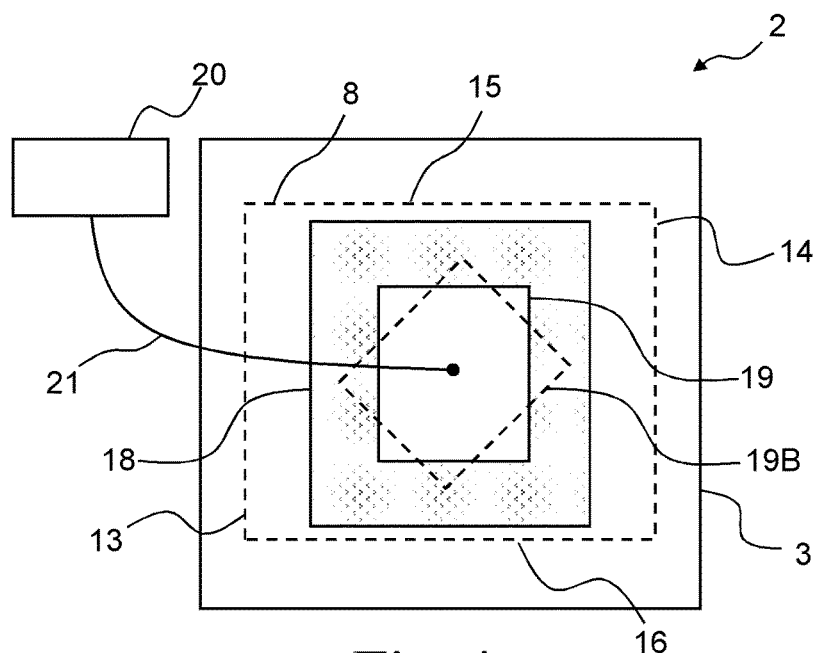

FIG. 4 schematically illustrates a top view of an exemplary RFID registration apparatus 2. In FIG. 4 the detector space 8 is seen with the first vertical side 13, the second vertical side 14, the third vertical side 15 and the fourth vertical side 16. For simplicity, the reflector surfaces are not shown in this figure. The first antenna 19 may be rotated to the position shown with dotted lines as 19B. This may be accomplished by utilizing a motor (not shown) for rotating the first antenna 19. The first antenna 19 may be rotated with any range of motion, and may be performed sequentially in one direction followed by another. Rotating the first antenna 19 allows for a dynamic change of the radiation pattern and/or polarization, thus minimizing the risk of RFID tags being orientated in a manner not receiving the electromagnetic radiation. Hence tilting the first antenna increases the precision and reliability of the reading even further.

Figure 5:
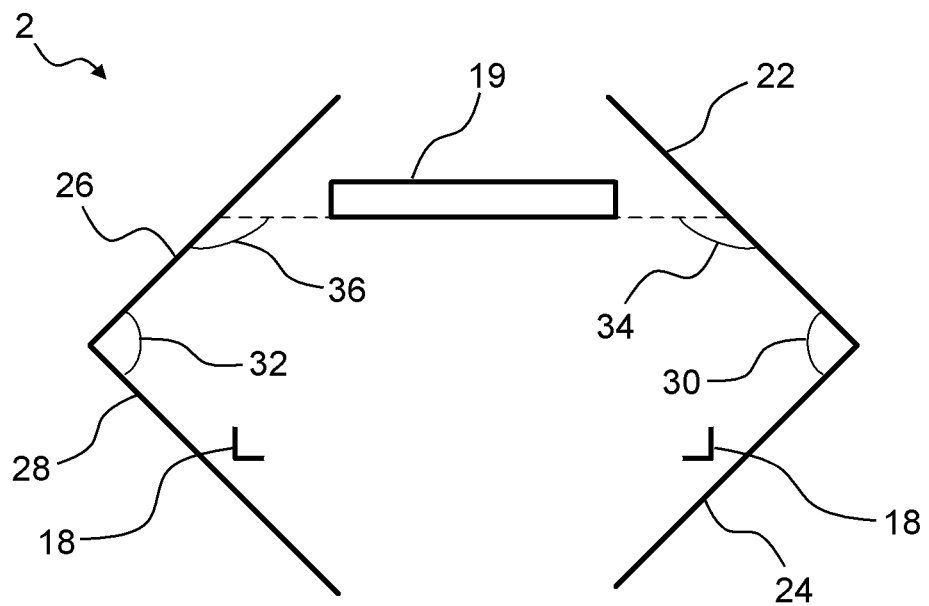

FIG. 5 schematically illustrates part of an exemplary RFID registration apparatus 2. The registration apparatus 2 spans a first angle 30 between the first primary 22 and the first secondary reflector surface 24. The registration apparatus 2 similarly spans a second angle 32 between the second primary 22 and the second secondary reflector surface 24. The first angle 30 and the second angle 32 are shown to be of the same magnitude, in other exemplary RFID registration apparatuses the first angle 30 and the second angle 32 may be of different magnitude. The first angle 30 and/or the second angle 32 may be less than 180 degrees, e.g. in the range of 70-140 degrees.

The first antenna 19 spans a first antenna angle 34 with the first primary reflector surface 24. The first antenna 19 similarly spans a second antenna angle 36 with the second primary reflector surface 26. The first antenna angle 34 and the second antenna angle 36 may be of the same magnitude. The first antenna angle 34 and/or the second antenna angle 36 may be more than 90 degrees, e.g. 120 degrees or 135 degrees or 150 degrees.

The first angle 30, the second angle 32, the first antenna angle 34, and the second antenna angle 36 are measured on the side of the surfaces that face the detector space 8 (FIG. 1)

Figure 6:
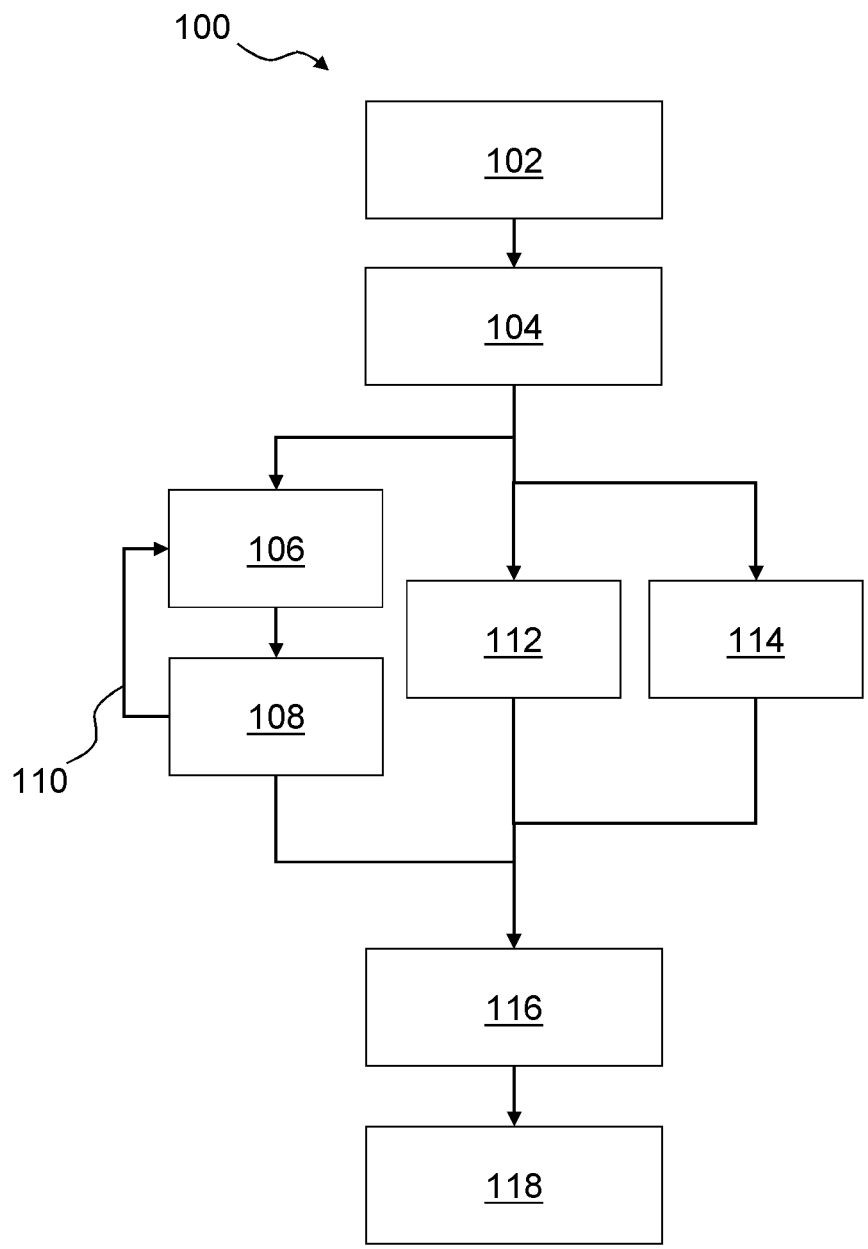
FIG. 6 illustrates a flow diagram of an exemplary method of operating an RFID registration apparatus.

FIG. 6 illustrates a flow chart of an exemplary method 100 for operating an RFID registration apparatus. The method 100 comprises placing a number of units in a receiver 102. Each unit comprises an RFID tag readable by the registration apparatus.

After placing the units in the receiver 102, the receiver is placed inside a detector space of a registration apparatus 104. From a first antenna placed at the top of the detector space, electromagnetic radiation is emitted 106 with a frequency adapted to the RFID tags to be registered. At the first antenna, electromagnetic radiation is received 108, the received electromagnetic radiation being emitted from RFID tags. Emitting electromagnetic radiation 106 and receiving electromagnetic radiation 108 is repeated 110 for a couple of seconds. Optionally, the first antenna may be tilted 112 and/or rotated 114 during the repeated 110 emitting 106 and receiving of electromagnetic radiation 108.

After receiving electromagnetic radiation 108, the method comprises identifying the RFID tags 116 from which electromagnetic radiation was received 108. Finally, the receiver is removed from the detector space 118.

LIST OF REFERENCES

2 RFID registration apparatus
3 housing
4 unit

6 RFID tag
8 detector space
10 top of detector space
12 bottom of detector space
13 first vertical side of detector space
14 second vertical side of detector space
15 third vertical side of detector space
16 fourth vertical side of detector space
17 tray
18 receiver
19, 19A, 19B antenna
20 reader
21 wire
22 first primary reflector surface
24 first secondary reflector surface
26 second primary reflector surface
28 second secondary reflector surface
30 first angle
32 second angle
34 first antenna angle
36 second antenna angle
100 method
102 placing of unit in receiver
104 place receiver inside detector space
106 emit electromagnetic radiation
108 receive electromagnetic radiation
110 repeat emitting and receiving
112 tilt the first antenna
114 rotate the first antenna
116 identify RFID tags
118 remove receiver from detector space

What is claimed is:

1. An RFID registration apparatus for registering units comprising RFID tags, the registration apparatus comprising:
a detector space comprising a top, a bottom and four vertical sides including a first vertical side and a second vertical side, wherein the second vertical side is opposite the first vertical side,
a receiver configured to receive a number of units and to be placed inside the detector space,
a first antenna configured to read the RFID tags by emitting and receiving electromagnetic radiation within a first frequency range, the first antenna is at the top of the detector space, and
at least four plane reflector surfaces, including a first primary reflector surface, a first secondary reflector surface, a second primary reflector surface and a second secondary reflector surface, each reflector surface is configured to reflect the electromagnetic radiation within the first frequency range,
wherein the first primary reflector surface is positioned to intersect the first vertical side and the top of the detector space, and the first secondary reflector surface is positioned to intersect the first vertical side and the bottom of the detector space, and the second primary reflector surface is positioned to intersect the second vertical side and the top of the detector space, and the second secondary reflector surface is positioned to intersect the second vertical side and the bottom of the detector space,
wherein the first primary reflector surface and the first secondary reflector surface span a first angle facing the detector space, and the second primary reflector surface and the second secondary reflector surface span a second angle facing the detector space, wherein the first angle and the second angle are in the range of 70-140 degrees.

2. The RFID registration apparatus according to claim 1, wherein the first angle and/or the second angle is a right angle.

3. The RFID registration apparatus according to claim 1, wherein the first primary reflector surface and the first antenna span a first antenna angle facing the detector space, and the second primary reflector surface and the first antenna span a second antenna angle facing the detector space, wherein the first antenna angle and/or the second antenna angle is more than 90 degrees.

4. The RFID registration apparatus according to claim 1, wherein the first primary reflector surface and/or the second primary reflector surface extends to a vertical position above the top of the detector space.

5. The RFID registration apparatus according to claim 1, wherein the first secondary reflector surface and/or the second secondary reflector surface extends to a vertical position below the bottom of the detector space.

6. The RFID registration apparatus according to claim 1, wherein the receiver is vertically positioned below a line from the first angle to the second angle.

7. The RFID registration apparatus according to claim 1, comprising a first motor configured to drive the receiver into and/or out of the detector space.

8. The RFID registration apparatus according to claim 1, comprising a second motor configured to change the orientation of the first antenna when reading the RFID tags.

9. The RFID registration apparatus according to claim 1, wherein the first antenna is tilted and/or rotated when reading the RFID tags.

10. The RFID registration apparatus according to claim 1, comprising a second antenna, the second antenna is positioned to intersect the top and a third vertical side of the detector space.

11. The RFID registration apparatus according to claim 1, wherein the first frequency range is in the range of 860-960 MHz.

12. The method for detecting and registering units comprising RFID tags, configured to respond to receiving electromagnetic radiation within a first frequency range, the method comprising the steps:
a. place a number of units in a receiver, each unit comprising an RFID tag,
b. place the receiver inside a detector space, the detector space including a top, a bottom and four vertical sides including a first vertical side and a second vertical side, wherein the second vertical side is opposite the first vertical side, and adjacent to the detector space is at least four plane reflector surfaces, including a first primary reflector surface, a first secondary reflector surface, a second primary reflector surface and a second secondary reflector surface, each reflector surface configured to reflect the electromagnetic radiation within the first frequency range, wherein the first primary reflector surface is positioned to intersect the first vertical side and the top of the detector space, and the first secondary reflector surface is positioned to intersect the first vertical side and the bottom of the detector space, and the second primary reflector surface is positioned to intersect the second vertical side and the top of the detector space, and the second secondary reflector surface is positioned to intersect the second vertical side and the bottom of the detector space, and a first antenna is at the top of the detector space, the first antenna configured to read the RFID tags by emitting and receiving the electromagnetic radiation within the first frequency range, the first primary reflector surface and the first secondary reflector surface span a first angle facing the detector space, and the second primary reflector surface and the second secondary reflector surface span a second angle facing the detector space, wherein the first angle and the second angle are in the range of 70-140 degrees, c. emit the electromagnetic radiation within the first frequency range from the first antenna, d. receive at the first antenna responses from the RFID tags in the receiver in the form of the electromagnetic radiation, e. repeat steps c and d one or more times, f. identify from the received responses which of the RFID tags responded, and g. remove the receiver from the detector space.

13. The method according to claim 12, wherein the first antenna is tilted and/or rotated during repeated emitting and receiving of the electromagnetic radiation.

14. The method according to claim 13, wherein the method further comprises comparing the identified RFID tags with values of a table, and reporting whether or not the identified RFID tags corresponds to values of the table.

15. The method according to claim 13, wherein the receiver is repositioned during repeated emitting and receiving of the electromagnetic radiation.

* * * * *